United States Patent
Alfiere

(10) Patent No.: US 9,913,868 B1
(45) Date of Patent: Mar. 13, 2018

(54) IMBIBABLE CANNABIS EXTRACT

(71) Applicant: Anthony James Alfiere, Scottsdale, AZ (US)

(72) Inventor: Anthony James Alfiere, Scottsdale, AZ (US)

( * ) Notice: Subject to any disclaimer, the term of this patent is extended or adjusted under 35 U.S.C. 154(b) by 190 days.

(21) Appl. No.: 14/677,614

(22) Filed: Apr. 2, 2015

Related U.S. Application Data

(60) Provisional application No. 61/974,358, filed on Apr. 2, 2014.

(51) Int. Cl.
| | |
|---|---|
| *A61K 36/00* | (2006.01) |
| *A61K 36/185* | (2006.01) |
| *A61K 31/352* | (2006.01) |
| *A61K 31/05* | (2006.01) |
| *A23L 1/30* | (2006.01) |

(52) U.S. Cl.
CPC .......... *A61K 36/185* (2013.01); *A23L 1/3002* (2013.01); *A61K 31/05* (2013.01); *A61K 31/352* (2013.01); *A23V 2002/00* (2013.01)

(58) Field of Classification Search
CPC ...................................... A61K 36/00
USPC ......................................... 424/725
See application file for complete search history.

(56) References Cited

U.S. PATENT DOCUMENTS 7,622,140 B2 * 11/2009 Whittle .............. B01D 11/0242
424/725

* cited by examiner

*Primary Examiner* — Michael V Meller
(74) *Attorney, Agent, or Firm* — Prudens Law LLC

(57) ABSTRACT

A method of producing an imbibable cannabis extract from cannabis plant matter is disclosed. The imbibable cannabis extract may comprise a flavored liquid extract of cannabinoid compounds. The method includes preparing a primary cannabis extract of cannabinoid compounds from dried cannabis plant matter including preparing a cannabis mash of dried cannabis plant matter and 91% ice cold isopropyl alcohol, collecting a cannabis/isopropyl alcohol filtrate, performing a paper filtration of collected cannabis/isopropyl alcohol filtrate, fractionally distilling the cannabis/isopropyl alcohol filtrate to remove the isopropyl alcohol, performing a decarboxylation reaction on the primary cannabis extract. A cannabis syrup may be prepared from the primary cannabis extract and a sorbate compound or blend. The imbible cannabis extract of cannabis syrup and a pasteurized mixture of 1.8 fluid ounces of water, 2.5 g erylite 400, and 0.5 mL flavoring per 2 fluid ounce serving size is prepared and filtered through a 0.05 micron filter.

10 Claims, 1 Drawing Sheet

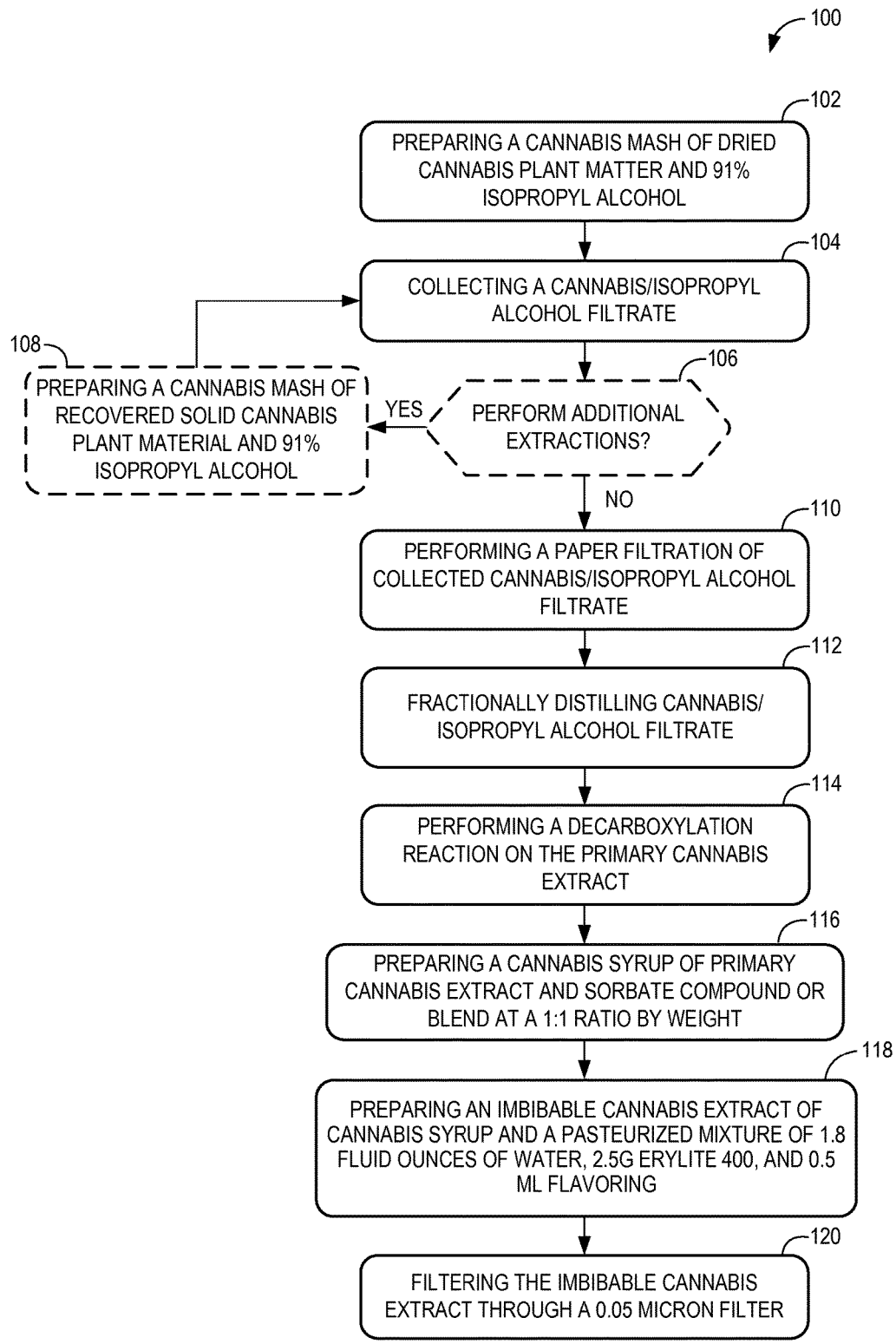

IMBIBABLE CANNABIS EXTRACT

CROSS-REFERENCE TO RELATED APPLICATIONS

This application claims the benefit of U.S. Provisional Patent Application No. 61/974,358, filed Apr. 2, 2014, and entitled "Imbibable Cannabis Extract", the complete contents of which are hereby incorporated herein by reference for all purposes.

BACKGROUND

Medical application of cannabis continues to increase. Currently, patients with a valid prescription can obtain medicinal cannabis from licensed dispensaries. Furthermore, recreational use of cannabis has become legal in certain jurisdictions. The individual may self-administer cannabis via smoking, vapor inhalation, and/or oral ingestion of cannabis infused food products.

SUMMARY

A method of producing an imbibable cannabis extract from cannabis plant matter is disclosed. The imbibable cannabis extract may comprise a flavored liquid extract of cannabinoid compounds. The method includes preparing a primary cannabis extract of cannabinoid compounds from dried cannabis plant matter including preparing a cannabis mash of dried cannabis plant matter and 91% ice cold isopropyl alcohol, collecting a cannabis/isopropyl alcohol filtrate, performing a paper filtration of collected cannabis/isopropyl alcohol filtrate, fractionally distilling the cannabis/isopropyl alcohol filtrate to remove the isopropyl alcohol, performing a decarboxylation reaction on the primary cannabis extract. A cannabis syrup may be prepared from the primary cannabis extract and a sorbate compound or blend. The imbible cannabis extract of cannabis syrup and a pasteurized mixture of 1.8 fluid ounces of water, 2.5 g erylite 400, and 0.5 mL flavoring per 2 fluid ounce serving size is prepared and filtered through a 0.05 micron filter.

BRIEF DESCRIPTION OF THE DRAWINGS

FIG. 1 illustrates a method of preparation of an imbibable cannabis extract according to an embodiment of this disclosure.

DETAILED DESCRIPTION

*Cannabis sativa* is an herbaceous plant of the Cannabaceae family. Humans have cultivated cannabis throughout recorded history. The various parts of the cannabis plant have been used in applications such as industrial fiber, food, religion, medicine, and, more controversially, recreational use.

Medical professionals may prescribe cannabis as a treatment for glaucoma, an antiemetic, an appetite stimulant, and as an analgesic for chronic pain, for example. Despite the increasing recognition of the medicinal applications of cannabis and recent jurisdictional authorization, individuals consuming cannabis must continually combat the social stigma associated with the public perception of recreational cannabis consumers.

Cannabis may be delivered through several means including smoking, inhalation of vaporized cannabis, or oral ingestion. Each method of delivery may include certain contraindications inherent to the delivery method. For example, inhalation of cannabis vapors requires a bulky apparatus to produce and collect the cannabis vapors for consumption. Cannabis for oral ingestion is often in the form of food products that require extensive preparation. Smoking cannabis includes medical contraindications such as the ingestion of carcinogenic compounds and irritation of respiratory tissues. Furthermore, an individual may have health conditions that may be exacerbated by cannabis smoke.

Another contraindication involves the variability of absorption of pharmacologically active cannabinoid compounds. Inhalation of cannabis smoke or vapor and oral ingestion of cannabis food products both exhibit variability in the absorbed cannabinoid compounds. The variability is due, in large part, to three factors, the amount of cannabis ingested, the concentration of cannabinoid compounds within the cannabis, and the method of absorption by the body. Furthermore, the process of digestion and first-pass processing of the cannabinoid compounds by the liver may significantly reduce the bioavailability of the cannabinoid compounds.

In addition to the contraindications discussed above, the adverse perception of cannabis consumers may negatively affect an individual's consumption of cannabis and/or adherence to the prescribed instructions of their medical professional. For example, an individual may choose not to smoke cannabis due to a desire to avoid inundation of their clothes and skin with the odor of cannabis smoke which their peers may find offensive. Aversions such as this may give the individual cause to seek alternative delivery methods of cannabis. For example, the desire for a more socially acceptable delivery method may lead an individual to attempt to prepare cannabis extracts which may be consumed more discretely. As the preparation of these extracts involves the use of volatile and potentially toxic solvents, the individual may risk the possibility of personal injury and property damage due to the explosive nature of the solvents required to extract the pharmacologically active compounds from cannabis. Furthermore, as the individual may not possess the technical expertise to properly prepare a safely ingestible cannabis extract, the pharmacological activity of the cannabis may be lost due to improper extraction methods or, in extreme cases, the extract may be toxic.

*Cannabis sativa* naturally produces a class of pharmacologically active compounds known as the Cannabinoids. The Cannabinoid family of compounds are a family of hydrophobic terpenophenolic compounds that may bind cannabinoid protein receptors expressed by cells throughout the body. Over 85 cannabinoid compounds have been isolated from *Cannabis sativa* including $\Delta^9$-tetrahydrocannabinol, cannabidiol, and the carboxylic acid species, tetrahydrocannabinolic acid and cannabidiolic acid. Both $\Delta^9$-tetrahydrocannabinol and cannabidiol have been shown to have pharmacologic activity in humans.

The pharmacological activity of $\Delta^9$-tetrahydrocannabinol (THC) is due to the binding and activation of the type 1-cannabinoid protein receptor. Studies have indicated that THC may have an analgesic activity, and a neuroprotective activity (i.e., reduce neuroinflammation, and stimulate neurogenesis). Other studies have identified THC as the primary psychoactive compound present in cannabis.

A second cannabinoid, cannabidiol (CBD), is also produced in abundance by the cannabis plant. CBD has also been shown to possess pharmacologic activities. Studies have indicated that CBD preferentially binds the type-2 cannabinoid receptor. Similar to THC, CBD also has been shown to have neuroprotective activity. Additionally, CBD has been shown to have analgesic, anticonvulsive, antiemetic, and antianxiety activities. Furthermore, CBD has been shown to mitigate the psychoactive effects of THC.

To date, the carboxylic acid species tetrahydrocannabinolic acid and cannabidiolic acid have shown no pharmacologic activity in humans. However, the tetrahydrocannabinolic acid and cannabidiolic acid species may be converted to $\Delta^9$-tetrahydrocannabinol and cannabidiol by the chemical process of decarboxylation. The process of decarboxylation requires the heating of tetrahydrocannabinolic acid and cannabidiolic acid to remove the carboxylic acid groups. The heating of cannabinoid compounds further serves to increase oral efficacy by enhancing the gastrointestinal absorption of the cannabinoid compounds.

Disclosed herein is a method of preparation of a non-carbonated imbibable cannabis extract. The imbibable cannabis extract may allow individuals to consume cannabis treatment while avoiding the adverse social stigma associated with cannabis use.

FIG. 1 illustrates a method 100 of preparation of an imbibable cannabis extract. Steps 102, 104, 106, 108, 110, and 112 of method 100 comprise preparing a primary cannabis extract of cannabinoid compounds from dried cannabis plant matter. It will be appreciated that other suitable methods of extracting cannabinoid compounds from dried cannabis plant matter may be used. Steps 114, 116, 118, 120 comprise the processing of the primary cannabis extract into an imbibable cannabis extract.

At 102, method 100 includes preparing a cannabis mash of dried cannabis plant matter and ice cold (~0° C./32° F.) 91% isopropyl alcohol. The dried cannabis plant material may include dried cannabis leaves, stems, flowers, and cuttings. The cannabis plant material may derive from any strain of the *Cannabis* plant, including *Cannabis sativa*, *Cannabis sativa forma indica*, *Cannabis ruderalis*, and any hybrid strain thereof. The cannabis mash is prepared by adding a volume of 3746 mL (1 gallon) of isopropyl alcohol for every 464 g (1 pound) of dried cannabis plant matter in a food grade high density polyethylene container. The mash may be prepared using a stainless steel mashing appliance which is used to both mix and grind the cannabis plant matter. The grinding of the cannabis plant matter serves to increase the surface area of the cannabis plant matter exposed to the isopropyl alcohol solvent and thus increase the efficiency of the extraction of the cannabinoid compounds.

At 104, method 100 includes collecting a cannabis/isopropyl alcohol filtrate. The cannabis/isopropyl alcohol filtrate is collected by filtering the cannabis mash through a 0.05 micron stainless steel filter. The filtered cannabis plant matter may be recovered and used for additional cannabis mash preparations.

At 106, method 100 may optionally include determining if additional extractions of cannabinoid compounds from the recovered cannabis plant matter are required. If additional extractions are to be performed, method 100 continues to 108. At 108, method 100 includes preparing a cannabis mash from the recovered solid cannabis plant matter and 91% isopropyl alcohol. The recovered cannabis plant matter may be mixed with an additional 3746 mL of ice cold 91% isopropyl alcohol to prepare another cannabis mash. The purpose of repeated mash preparations using recovered cannabis plant matter is to increase the efficiency of extraction of cannabinoid compounds from the dried cannabis plant matter. Each subsequent preparation will include collection of a volume of cannabis/isopropyl alcohol filtrate as discussed above. The collected volumes of cannabis/isopropyl alcohol filtrate may be combined prior to fractional distillation.

If additional extractions are not required, method 100 proceeds to 110, which includes performing a paper filtration of the collected cannabis/isopropyl alcohol filtrate. The cannabis/isopropyl alcohol filtrate is passed through a paper filter to remove from the cannabis/isopropyl alcohol filtrate any fine particulate and/or suspended solids that may be produced during the mashing process.

At 112, method 100 includes performing a fractional distillation of the cannabis/isopropyl alcohol filtrate. Fractional distillation, or separation of a liquid mixture by boiling point, may be performed by heating the cannabis/isopropyl alcohol filtrate to 76-85° C. (170-185° F.) in an oil bath until the isopropyl alcohol is completely removed by boiling. In addition to removal of the isopropyl alcohol, the fractional distillation may also concentrate the extract. The fractional distillation completes the preparation of the primary cannabis extract.

At 114, method 100 includes performing a decarboxylation reaction on the primary cannabis extract. The decarboxylation reaction includes stirring the primary cannabis extract with a glass stirring rod for 7 minutes at a temperature of 145° C. (293° F.). Heating the primary cannabis extract to this temperature functions to convert the carboxylic acids tetrahydrocannabinolic acid and cannabidiolic acid to $\Delta^9$-tetrahydrocannabinol and cannabidiol as discussed above. Furthermore, the decarboxylation reaction also serves to increase the gastrointestinal absorption of the cannabinoid compounds within the decarboxylated primary cannabis extract. As the temperature required for the decarboxylation reaction is above the boiling point of water, an additional volume of water may be added upon completion of the decarboxylation reaction.

At 116, method 100 includes preparing a cannabis syrup of primary cannabis extract and polysorbate 20 mixed at a 1:1+/−10% ratio by weight. For example, 100 g polysorbate 20 will be added to 100 g primary cannabis extract to prepare a cannabis syrup. It will be appreciated that the ratio of primary cannabis extract to polysorbate 20 may be adjusted as determined by method testing and optimization. The cannabis syrup is stirred for 3 minutes at 60-69° C. (140-155° F.). In other embodiments, polysorbate 20 may be replaced with another compound in the sorbate family, including polysorbate 60 and polysorbate 80, combinations of sorbate compounds, or blends that mix sorbate compounds with other materials.

At 118, method 100 includes preparing an imbibable cannabis extract of cannabis syrup and a pasteurized mixture of 1.8 fluid ounces of water, 2.5 g erylite 400, and 0.5 mL of flavoring. The quantity of cannabis syrup added to the pasteurized water/erylite 400/flavoring mixture may be sufficient to obtain a dosage of 5-10 mg of tetrahydrocannabinol per imbibable cannabis extract. Sugar could also be used in place of or in addition to erylite 400. It will be appreciated that the quantity of cannabis syrup may also be measured by volume or by mass (i.e., 0.145 g of cannabis syrup). The imbibable cannabis extract may be mixed by shaking, stirring, or any other suitable method of mixing to suspend the cannabis syrup within the pasteurized mixture, and an emulsifier may be further added so as to form an emulsified concentrate. It will be further appreciated that the final dosage of tetrahydrocannabinol may be adjusted for any suitable purpose such as optimal efficacy, and/or compliance with governing ordinances, for example. Further, it will be appreciated that the composition of the pasteurized water, erylite 400, and flavoring mixture may be varied to obtain a more palatable flavor of the final product.

Additionally, the water may be acidified to enhance the mixing process and to inhibit microbial growth within the imbibable cannabis extract. The water may be acidified by adding a sufficient quantity of acid such as citric acid, ascorbic acid, or any other suitable food grade acid, to adjust the pH of the water to a range of pH 3.0-4.5.

At 120, method 100 includes filtering the imbibable cannabis extract through a 0.05 micron filter to remove unmixed cannabis syrup and any suspended solids.

As this invention may be embodied in several forms without departing from the spirit of essential characteristics thereof, the present embodiments are therefore illustrative and not restrictive, since the scope of the invention is defined by the appended claims rather than by the description preceding them, and all changes that fall within metes and bounds of the claims, or equivalence of such metes and bounds thereof are therefore intended to be embraced by the claims.

The invention claimed is:

1. A cannabis extract, the cannabis extract containing a flavored liquid extract of cannabinoid compounds, the cannabis extract prepared by a method comprising:
   (a) preparing a primary cannabis extract of cannabinoid compounds from dried cannabis, the preparation of the primary cannabis extract including:
       preparing a cannabis mash of dried cannabis and ice cold 91% isopropyl alcohol wherein the cannabis mash is prepared by mixing the dried cannabis and ice cold 91% isopropyl alcohol at a weight to volume ratio of 464 g to 3746 mL;
       collecting a cannabis/isopropyl alcohol filtrate by filtering the cannabis mash through a 0.05 micron stainless steel filter;
       performing a paper filtration of collected cannabis/isopropyl alcohol filtrate;
       fractionally distilling the cannabis/isopropyl alcohol filtrate to remove the isopropyl alcohol;
   (b) performing a decarboxylation reaction on the primary cannabis extract;
   (c) preparing a cannabis syrup of the primary cannabis extract and sorbate compound or blend at a 1:1+/−10% ratio by weight;
   (d) preparing an cannabis extract of cannabis syrup and a pasteurized mixture of 1.8 fluid ounces of water, 2.5 g erylite 400, and 0.5 mL flavoring per 2 fluid ounce service size; and
   (e) filtering the cannabis extract through a 0.05 micro filter.

2. The cannabis extract of claim 1, wherein the dried cannabis includes dried leaves, stems, or flowers.

3. The cannabis extract of claim 1, wherein collecting the cannabis/isopropyl alcohol filtrate includes:
   filtering the cannabis mash through a 0.05 micron stainless steel filter;
   recovering the cannabis from the filer, and
   collecting the cannabis/isopropyl alcohol filtrate.

4. The cannabis extract of claim 1, further comprising performing additional preparations of the cannabis mash, the additional preparations using cannabis recovered from a previous filtration of the cannabis mash and a fresh 3746 mL volume of ice cold 91% isopropyl at 0° C.

5. The cannabis extract of claim 1, wherein the decarboxylation reaction of the primary cannabis extract includes stirring the primary cannabis extract with a glass rod for 7 minutes at a temperature of 145° C.

6. The cannabis extract of claim 1, wherein preparing the cannabis syrup further includes stirring the primary cannabis extract/sorbate compound mixture or primary cannabis extract/sorbate blend mixture for 3 minutes at a temperature of 64° C.

7. The cannabis extract of claim 1, wherein a quantity of the cannabis syrup is sufficient to obtain 5-10 mg of tetrahydrocanabinol per cannabis extract.

8. The cannabis extract of claim 1, wherein the quantity of cannabis syrup is 0.145 g.

9. A cannabis extract, the cannabis extract containing a flavored liquid extract of cannabinoid compounds, the cannabis extract prepared by a method comprising:
   (a) preparing a primary cannabis extract of cannabinoid compounds from dried cannabis, the preparation of the primary cannabis extract including:
       preparing a cannabis mash of dried cannabis and ice cold 91% isopropyl alcohol;
       collecting a cannabis/isopropyl alcohol filtrate;
       performing a paper filtration of collected cannabis/isopropyl alcohol filtrate;
       fractionally distilling the cannabis/isopropyl alcohol filtrate to remove the isopropyl alcohol;
   (b) performing a decarboxylation reaction on the primary cannabis extract;
   (c) preparing a cannabis syrup of primary cannabis extract and sorbate compound or blend at a 1:1+/−10% ratio by weight;
   (d) preparing an cannabis extract of cannabis syrup and a pasteurized mixture of 1.8 fluid ounces of water at a pH of 4.0, 2.5 g erylite 400, and 0.5 mL flavoring per 2 fluid ounce service size, wherein a quantity of the cannabis syrup is sufficient to obtain 5-10 mg of tetrahydrocannabinol per cannabis extract; and
   (e) filtering the cannabis extract through a 0.05 micro filter.

10. The cannabis extract of claim 9, wherein quantity of cannabis syrup is 0.145 g.

\* \* \* \* \*